US005689018A

United States Patent [19]
Klingler et al.

[11] Patent Number: 5,689,018
[45] Date of Patent: Nov. 18, 1997

[54] PROCESS FOR THE PRODUCTION OF DINITROTOLUENE

[75] Inventors: Uwe Klingler, Dormagen; Thomas Schieb, Rörath; Gerhard Wiechers, Leverkusen, all of Germany; Jürgen Zimmermann, Walnut Creek, Calif.

[73] Assignee: Bayer Aktiengesellschaft, Leverkusen, Germany

[21] Appl. No.: 510,803

[22] Filed: Aug. 3, 1995

[30] Foreign Application Priority Data

Aug. 11, 1994 [DE] Germany ............... 44 28 462.4

[51] Int. Cl.[6] ............................................ C07C 205/00
[52] U.S. Cl. ...................... 568/934; 568/927; 568/932
[58] Field of Search ............................ 568/934, 932, 568/927

[56] References Cited

U.S. PATENT DOCUMENTS

| | | | |
|---|---|---|---|
| 3,928,475 | 12/1975 | Dassel | 260/645 |
| 4,021,498 | 5/1977 | Alexanderson et al. | 260/645 |
| 4,091,042 | 5/1978 | Alexanderson et al. | 260/645 |
| 4,367,347 | 1/1983 | Sawicki et al. | 568/934 |
| 4,453,027 | 6/1984 | Vaidyanathan | 568/937 |
| 4,663,490 | 5/1987 | Gerken et al. | 568/934 |
| 5,345,012 | 9/1994 | Schieb et al. | 568/934 |

FOREIGN PATENT DOCUMENTS 436 443   7/1991   European Pat. Off. .

Primary Examiner—Marianne M. Cintins
Assistant Examiner—Dwayne C. Jones
Attorney, Agent, or Firm—Joseph C. Gil; Lyndanne M. Whalen

[57] ABSTRACT

Dinitrotoluene is produced from toluene and nitric acid in the presence of sulfuric acid in a two stage process in the first stage, toluene and nitric acid are reacted under isothermal conditions in amounts such that mononitrotoluene is produced. The reaction mixture is then separated into an organic phase and an acid phase. The organic phase is then further reacted with nitric acid under adiabatic conditions to produce dinitrotoluene. The reaction mixture is then separated into an organic phase and an acid phase. Dinitrotoluene is recovered from the organic phase. After at least 5% by weight water is removed from the acid phase and sufficient nitric acid to replace that consumed during the nitration reaction has been added, the acid phase may be recycled.

4 Claims, No Drawings

PROCESS FOR THE PRODUCTION OF DINITROTOLUENE

BACKGROUND OF THE INVENTION

The present invention relates to a two-stage process for the production of dinitrotoluene from toluene and nitric acid in the presence of sulfuric acid.

Dinitrotoluene (DNT) is an intermediate product in tolylene diisocyanate (TDI) production. DNT is obtained industrially by reacting toluene with a nitrating acid which is a mixture of nitric and sulfuric acid (DE-B 1 468 362; T. Urbanski, *Chemistry and Technology of Explosives*, Pergamon Press (1964); Ullmanns *Encyklopädie der technischen Chemie* [Encyclopedia of Industrial Chemistry], 4th edition, vol. 17, p. 392, Verlag Chemie, Weinheim (1979)). In this industrial process, mononitrotoluene (MNT) is first prepared by reacting toluene with a dilute nitrating acid. After separating the depleted sulfuric acid (hereinafter referred to as "spent acid"), this MNT is further reacted to form DNT in a second stage with a more highly concentrated nitrating acid. Both reaction stages are conducted isothermally, i.e., with cooling. Because nitration is a very strongly exothermic reaction, the expense for the requisite cooling is high.

In the two-stage process, two spent acids are generated. These spent acids are recycled after nitric acid has been added in an amount sufficient to replace that used in the nitration reaction. The spent acid from the second stage may be recycled directly if this spent acid is still sufficiently concentrated that it can be reused in the first stage without being first reconcentrated. If the spent acid from the first stage of the nitration reaction is to be reused, it must be reconcentrated to remove at least the water of reaction. The most commonly used processes for removal of this water are the Pauling process (Bodenbrenner, von Piessen, Vollmüller, *Dechema monograph* 86 (1980), 197) and concentration by evaporation under vacuum (Winnacker, Küchler, *Chem. Technol.*, Vol. 2, *Anorg. Technol,* 1, 4th edition (1982), pp. 70 to 72). A common feature of each of these processes is their high energy input requirement and consequent demand and cost.

A further disadvantage of the above-described industrial process is the preference for expensive highly concentrated nitric acid to reconstitute the nitrating acid from the spent acids. Dilute nitric acid (e.g., azeotropic or weak acid) which is markedly cheaper can, in principle, be used, but the additional energy requirement is considerable.

These disadvantages are not specific to toluene nitration but are also relevant to the nitration of other aromatic materials. Researchers have therefore long sought to improve the nitration process.

Benzene mononitration under adiabatic conditions does result in an energy improvement. Adiabatic reaction also made it possible to use dilute nitric acids in a way which is simple in terms of process engineering. Adiabatic nitration is therefore currently being practiced on a large industrial scale. (See, for example, U.S. Pat. Nos. 3,928,475; 4,021,498; 4,091,042; and U.S. Pat. No. 4,453,027; and EP-A 436,443.)

Adiabatic process conditions may also be applied to the production of dinitroaromatics (EP-A 597,361 ). In this case, an aromatic compound such as toluene is reacted with nitrating acid in a single stage to form DNT. It is possible by using nitrating acids of a specific composition to operate the nitration process adiabatically and to conserve the heat of reaction within the system. It is no longer necessary to cool the process as in the conventional isothermal process, thus saving expensive cooling power. After phase separation, the hot spent acid is atomized under vacuum, and the heat of reaction from the process is used to reconcentrate the spent acid. Because the reaction is adiabatic and the associated reaction temperature is high, dilute nitric acids may be used in this process. Depending on the quality of nitric acid used, little or no heating is required in the reconcentration step.

The disadvantage of this process is the high proportion of ortho-DNT produced. The amount of ortho-DNT produced is higher than that produced by the isothermal process. This higher ortho-isomer content is attributable to the higher reaction temperature during nitration. Ortho-DNT is an undesirable mixture of DNT isomers having nitro groups in the ortho position (i.e., 2,3- and 3,4-DNT), which is of no use in TDI manufacture. It is therefore considered to be a waste product which must be separated at considerable expense.

The classic isothermal nitration process also produces a certain proportion of ortho-DNT, but that proportion is not as high as that obtained in the known adiabatic process. The ortho-DNT isomers are normally separated after hydrogenation at the amine stage. This requires a highly efficient separating column because the difference between the boiling point of the ortho-substituted amine and the desired product amine is not very great. Consequently, a high reflux ratio which drives distillation costs up appreciably is required. Because there is no use for the ortho-amine, once separated, increased production of this amine is equivalent to lost product yield. Increased production of ortho-DNT results in additional costs in terms of hydrogenation and destruction of the unwanted product.

Another disadvantage of the known adiabatic nitration process is the need for spent acid reconcentration. This spent acid contains dissolved organic compounds, including substantially dissolved DNT. These organic compounds are steam-volatile and are to a large extent evaporated during reconcentration of the spent acid. Modern, safe vacuum processes require low condensation conditions for the evaporated water. At these temperatures, DNT crystallizes and causes fouling of the condensation system.

DNT crystallization is, admittedly, also a problem with the isothermal process. However, this problem is solved in the isothermal process by injecting MNT into the hot exhaust gases (DE-A 3,409,719). The exhaust vapor condensate is in this way maintained in a fluid state and blockages are avoided. This is not possible with the known adiabatic process.

SUMMARY OF THE INVENTION

It is an object of the present invention to provide an improved process for the dinitration of aromatic compounds, in particular toluene.

It is also an object of the present invention to provide a dinitration process in which the ortho-isomer content of the dinitration product is reduced.

It is another object of the present invention to provide a process for dinitrating organic materials in which the heat of the nitration reaction is used and in which dilute nitric acid may be employed.

It is a further object of the present invention to provide a process for dinitrating aromatic compounds in which the spent acid may be reconcentrated without fouling the condensation system.

These and other objects which will be apparent to those skilled in the art are accomplished by reacting toluene with a nitrating acid isothermally in a first stage to produce mononitrotoluene, separating the reaction mixture into a spent acid phase and an organic phase and nitrating the organic phase containing mononitrotoluene with nitrating acid under adiabatic conditions to produce dinitrotoluene. The reaction mixture is then separated into a spent acid phase and an organic phase containing dinitrotoluene. At least 5% of the water present in the acid phase generated in the second stage of this process is removed before that acid phase is recycled.

DETAILED DESCRIPTION OF THE INVENTION

The present invention relates to a two-stage process for the continuous production of dinitrotoluene in which dinitrotoluene isomer mixtures having a low proportion of ortho-DNT are obtained. In the first stage of this process, toluene and nitrating acid (1) comprising (a) from about 80 to about 100% by weight (based on the total weight of nitrating acid (1)) inorganic materials which include (i) from about 60 to about 90% by weight (based on the total weight of (1)(a)) sulfuric acid, (ii) from about 1 to about 20% by weight (based on the total weight of (1)(a)) flittic acid and at least 5% by weight (based on total weight of (1)(a)) water and (b) from 0 to about 20% by weight (based on the total weight of nitrating acid (1)) organic materials which comprise (i) from about 70 to about 100% by weight (based on the total weight of (1)(b)) nitrotoluene isomers and (ii) from 0 to about 30% by weight (based on the total weight of (1)(b)) by-products of the nitration reaction, are reacted isothermally in a continuously operated reactor at a temperature of from about 0° to about 100° C. The molar ratio of nitric acid to toluene in this first stage is at least 0.7:1 but no greater than 1.2:1. The resultant reaction mixture containing mononitrotoluene is then separated into an organic phase and an acid phase by phase separation. The organic phase which is predominantly mononitrotoluene (MNT) is then reacted under adiabatic conditions at temperatures of from about 20° to about 200° C., preferably from about 40° to about 180° C., most preferably from about 60° to about 170° C., with a nitrating acid (2) comprising (a) from about 80 to 100% by weight (based on the total weight of nitrating acid (2)) inorganic constituents which are composed of (i) from about 60 to about 90% by weight (based on the total weight of (2)(a)) sulfuric acid, (ii) from about 1 to about 20% by weight (based on total weight of (2)(a)) nitric acid and at least 5% by weight (based on total weight of (2)(a)) water and (b) from 0 to about 20% by weight (based on the total weight of nitrating acid(2)) organic constituents which comprise (i) from about 70 to about 100% by weight (based on total weight of (2)(b)) nitrotoluene isomers and (ii) from 0 to about 30% by weight (based on the total weight of (2)(b)) by-products of the nitration process. The molar ratio of nitric acid to mononitrotoluene in this second stage is at least 0.7:1 but no greater than 1.2:1. The reaction mixture is then separated into an organic phase containing dinitrotoluene and an acid phase by phase separation. At least 5% of the water is removed from the acid phase from the second stage, e.g., by distillation (preferably by flash evaporation), optionally with simultaneous supply of heat. 50–100% by weight nitric acid is then added to this reconcentrated acid phase and the acid phase is recycled continuously into the nitration reaction.

Mononitrotoluene (MNT) from the first stage is preferably added to the exhaust vapors from the reconcentration of the acid phase from the second stage prior to condensation of those exhaust vapors. The quantity of MNT added is selected so that the exhaust vapor condensate will run off in the fluid state and will not form solid deposits. This may generally be achieved when the ratio by weight of MNT to DNT in the exhaust vapor condensate from the organic phase is from about 2:1 to about 10:1. The organic constituents of the exhaust vapor condensate are recycled into the first or the second nitration stage after phase separation.

It is preferred that at least 5% by weight of the water in the spent acid phase recovered after the first stage of the process of the present invention be removed (e.g., by distillation) and recycled continuously into the reaction after the addition of 50 to 100% by weight nitric acid.

It is surprising that a low ortho-DNT content is achieved when the first stage nitration (to form mononitrotoluene) is conducted isothermally and the second stage (from MNT to dinitrotoluene) is conducted adiabatically. The process of the present invention produces DNT having ortho-isomer contents which are no greater than those obtained in the conventional isothermal process ($\leq 4.5\%$ by weight). The use of adiabatic conditions in the second stage utilizes the heat of reaction and makes it possible to use dilute nitric acid.

The process of the present invention is also particularly advantageous because existing old, two-stage, isothermal nitration plants can be readily converted to the adiabatic technology. Full use can be made of the isothermal first stage technology which is already in place in the existing plant. Only the second stage of an existing plant need be converted to adiabatic technology.

Having thus described our invention, the following Examples are given as being illustrative thereof. All percentages given in these Examples are percentages by weight.

EXAMPLES

Example 1

92.14 g/h toluene (1 mol/h) and 895 g/h (1.08 mol/h) nitrating acid composed of 71.9% sulfuric acid, 7.6% nitric acid, and 20.5% water were continuously reacted isothermally in a reactor at 40° C. with cooling. The phases of this reaction mixture were separated, the spent acid was reconcentrated under vacuum and after adding sufficient 60% nitric acid to replace that consumed in the nitration reaction was recycled into the reaction. The separated organic phase was continuously reacted under adiabatic conditions with 1890 g/h (1.08 mol/h) nitrating acid composed of 77.9% sulfuric acid, 3.6% nitric acid, and 18.5% water at a starting temperature of approximately 120° C. (achieved by mixing with the returned, reconcentrated spent acid from the adiabatic nitration step). The reaction mixture was then separated into an acid phase and an organic phase by phase separation. The acid phase was reconcentrated under vacuum. In order to avoid deposit formation in the condensation section of the processing equipment, 9 g/h MNT from the first nitration stage were added to the superheated exhaust vapors from the evaporator. The reconcentrated spent acid was recycled into the adiabatic nitration step after 60% nitric acid had been added in an amount sufficient to replace the nitric acid consumed in the nitration reaction. The organic constituents of the exhaust vapor condensate were also recycled. 180 g/h (99%) dinitrotoluene isomer mixture were isolated. The ortho-DNT content is 4.1% by weight.

Example 2

92.14 g/h toluene (1 mol/h) and 1063 g/h (1.08 mol/h) nitrating acid composed of 72.5% sulfuric acid, 6.4% nitric acid, and 21.1 % water were continuously reacted isothermally in a reactor at 40° C. with cooling. The reaction mixture was separated into an acid phase and an organic phase. The spent acid phase was reconcentrated under vacuum and after 60% nitric acid had been added to replace the nitric acid consumed in the nitration reaction was recycled into the reaction. The separated organic phase was continuously reacted under adiabatic conditions with 586.6 g/h (1.08 mol/h) nitrating acid composed of 73.6% sulfuric acid, 11.6% nitric acid and 14.8% water at a starting temperature of approximately 60° C. The reaction mixture was then separated into an acid phase and an organic phase. The acid phase was reconcentrated under vacuum. In order to avoid deposit formation in the condensation section, 4.5 g/h MNT from the first nitration stage were added to the superheated exhaust vapors from the evaporator. The reconcentrated spent acid was recycled into the adiabatic nitration step after 98.5% nitric acid was added in an amount sufficient to replace the nitric acid consumed in the nitration reaction. The organic constituents of the exhaust vapor condensate were also recycled into the adiabatic nitration step. 180 g/h (99%) dinitrotoluene isomer mixture were isolated. The ortho-DNT content is 4.0 % by weight.

Example 3

92.14 g/h toluene (1 mol/h) and 895 g/h (1.08 mol/h) nitrating acid composed of 71.9% sulfuric acid, 7.6% nitric acid and 20.5% water were continuously reacted isothermally in a reactor at 40° C. with cooling. The reaction mixture was separated into an organic phase and an acid phase. The spent acid was reconcentrated under vacuum and after 60% nitric acid had been added in an amount sufficient to replace that which was consumed in the nitration reaction was recycled into the reaction. The separated organic phase was continuously reacted under adiabatic conditions with 1173.1 g/h (1.08 mol/h) nitrating acid composed of 76.9% sulfuric acid, 5.8% nitric acid and 17.3% water at a starting temperature of approximately 100° C. The reaction mixture was separated into an acid phase and an organic phase. The acid phase was then reconcentrated under vacuum. In order to avoid deposit formation in the condensation section, 7 g/h MNT from the first nitration stage were added to the superheated exhaust vapors from the evaporator. The reconcentrated spent acid was recycled into the adiabatic nitration step after 68% nitric acid was added in an amount sufficient to replace that which was consumed in the nitration reaction. The organic constituents of the exhaust vapor condensate were also recycled to the adiabatic nitration step. 180 g/h (99%) dinitrotoluene isomer mixture were isolated.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims. The ortho-DNT content is 4.1% by weight.

What is claimed is:

1. A two-stage process for the continuous production of isomer mixtures of dinitrotoluene comprising A) reacting
   1) toluene with
   2) nitrating acid composed of
      a) from 80 to 100% by weight of inorganic materials which include:
         (i) from about 60 to about 90% by weight of sulfuric acid,
         (ii) from about 1 to about 20% by weight of nitric acid, and
         (iii) at least 5% by weight of water and
      b) from 0 to about 20% by weight of organic materials which include:
         (i) from about 70% by weight of isomers of nitrotoluene and
         (ii) from 0 to about 30% by weight of by-products of the nitration reaction
   isothermally in a continuously operated reactor at a temperature of from about 0 to about 100° C. in amounts such that the molar ratio of nitric acid to toluene is at least 0.7:1 but no greater than 1.2:1, B) separating the reaction mixture from A) into an organic phase and an acid phase, C) reacting the organic phase separated in B) under adiabatic conditions at a temperature of from about 20 to about 200° C. with a nitrating acid which is made up of:
   a) from about 80 to about 100% by weight inorganic materials which include:
      (i) from about 60 to about 90% by weight sulfuric acid,
      (ii) from about 1 to about 20% by weight nitric acid, and
      (iii) at least 5% by weight water, and
   b) from 0 to about 20% by weight organic materials which include:
      (i) from about 70 to about 100% by weight isomers of nitrotoluene and
      (ii) from 0 to about 30% by weight by-products of the nitration reaction, in amounts such that the molar ratio of nitric acid to mononitrotoluene is at least 0.7:1 but no greater than 1.2:1, D) separating the reaction mixture from C) into an organic phase and an acid phase, E) removing at least 5% by weight of water from the acid phase separated in D), F) adding 50–100% nitric acid to the acid phase from E) and G) recycling the acid phase from F).

2. The process of claim 1 in which step D) is carried out by distillation.

3. The process of claim 1 in which step D) is carried out by flash evaporation.

4. The process of claim 1 in which step D) is carried out by flash evaporation with the simultaneous supply of heat.

* * * * *